United States Patent
Kwon et al.

(10) Patent No.: US 9,486,528 B2
(45) Date of Patent: *Nov. 8, 2016

(54) STABLE PHARMACEUTICAL FORMULATION FOR ORAL ADMINISTRATION COMPRISING LEVOCETIRIZINE OR A PHARMACEUTICALLY ACCEPTABLE SALT THEREOF, AND MONTELUKAST OR A PHARMACEUTICALLY ACCEPTABLE SALT THEREOF

(71) Applicant: HANMI PHARM. CO., LTD., Hwaseong-si, Gyeonggi-do (KR)

(72) Inventors: Taek Kwan Kwon, Suwon-si (KR); Dong Ho Kim, Seoul (KR); Kyeong Soo Kim, Suwon-si (KR); Yong Il Kim, Suwon-si (KR); Jae Hyun Park, Suwon-si (KR); Jong Soo Woo, Suwon-si (KR)

(73) Assignee: HANMI PHARM. CO., LTD, Hwaseong-si (KR)

( * ) Notice: Subject to any disclaimer, the term of this patent is extended or adjusted under 35 U.S.C. 154(b) by 0 days.
This patent is subject to a terminal disclaimer.

(21) Appl. No.: 14/370,258
(22) PCT Filed: Jan. 4, 2013
(86) PCT No.: PCT/KR2013/000057
§ 371 (c)(1),
(2) Date: Jul. 2, 2014
(87) PCT Pub. No.: WO2013/103262
PCT Pub. Date: Jul. 11, 2013

(65) Prior Publication Data
US 2014/0356422 A1 Dec. 4, 2014

(30) Foreign Application Priority Data
Jan. 6, 2012 (KR) .................. 10-2012-0001954

(51) Int. Cl.
*A61K 47/12* (2006.01)
*A61K 31/4704* (2006.01)
(Continued)

(52) U.S. Cl.
CPC ............... *A61K 47/12* (2013.01); *A61K 9/14* (2013.01); *A61K 9/2013* (2013.01);
(Continued)

(58) Field of Classification Search
CPC .... A61K 47/12; A61K 45/06; A61K 9/4808; A61K 9/14; A61K 9/2013; A61K 9/2095; A61K 9/4858; A61K 9/2018; A61K 9/2027; A61K 9/2054; A61K 9/2059; A61K 9/2866; A61K 2300/00; A61K 31/4704; A61K 31/496; A61K 31/47; A61K 31/4965; A61K 31/495
See application file for complete search history.

(56) References Cited

U.S. PATENT DOCUMENTS 9,220,704 B2 * 12/2015 Kim .................. A61K 31/4178
2001/0025040 A1 9/2001 Poppe et al.
2003/0055077 A1 3/2003 Jones

FOREIGN PATENT DOCUMENTS

EP  1 274 457 B1  11/2005
GB  1204580 A  9/1970
(Continued)

OTHER PUBLICATIONS

Rathod et al ("FDC of montelukast with levocetirizine : focus on bilayer technology" in Journal of the Indian Medical Association, Aug. 2009.*

(Continued)

*Primary Examiner* — Blessing M Fubara
(74) *Attorney, Agent, or Firm* — Sughrue Mion, PLLC (57) ABSTRACT

The present invention relates to a pharmaceutical formulation for oral administration for preventing or treating allergic rhinitis or asthma, which comprises: (a) a first particle part comprising levocetirizine or a pharmaceutically acceptable salt thereof and an organic acid; and (b) a second particle part comprising montelukast or a pharmaceutically acceptable salt thereof. The pharmaceutical formulation according to the present invention comprises an organic acid as a stabilizing agent, which can effectively inhibit the production of levocetirizine and montelukast related substances, and thus, show good stability.

10 Claims, 2 Drawing Sheets

Levocetirizine layer

Montelukast layer (51) Int. Cl.
 *A61K 31/4965*    (2006.01)
 *A61K 31/496*     (2006.01)
 *A61K 31/495*     (2006.01)
 *A61K 9/48*       (2006.01)
 *A61K 9/14*       (2006.01)
 *A61K 9/20*       (2006.01)
 *A61K 31/47*      (2006.01)
 *A61K 45/06*      (2006.01)
 *A61K 9/28*       (2006.01)

(52) U.S. Cl.
 CPC .......... *A61K 9/2095* (2013.01); *A61K 9/4808* (2013.01); *A61K 9/4858* (2013.01); *A61K 31/47* (2013.01); *A61K 31/4704* (2013.01); *A61K 31/495* (2013.01); *A61K 31/496* (2013.01); *A61K 31/4965* (2013.01); *A61K 45/06* (2013.01); *A61K 9/2018* (2013.01); *A61K 9/2027* (2013.01); *A61K 9/2054* (2013.01); *A61K 9/2059* (2013.01); *A61K 9/2866* (2013.01)

(56) References Cited

FOREIGN PATENT DOCUMENTS

| | | |
|---|---|---|
| KR | 10-2002-0083161 A | 11/2002 |
| KR | 10-0910848 B1 | 8/2009 |
| WO | 0178697 A2 | 10/2001 |
| WO | WO 01/78697 A2 * | 10/2001 |
| WO | 2007078110 A1 | 7/2007 |
| WO | WO 2007/078110 A1 * | 7/2007 |
| WO | WO 2010/107404 A1 * | 1/2010 |
| WO | 2010/107404 A1 | 9/2010 |
| WO | 2013/012199 A1 | 1/2013 |

OTHER PUBLICATIONS

Mayo Clinic Asthma Prevention, Jan. 7, 2014.*
European Patent Office, Communication dated Jul. 15, 2015 issued in corresponding European application No. 13733789.5.
Patent Office of Saudi Arabia; Communication dated Apr. 29, 2015 in counterpart Application No. 113340174.
International Searching Authority—International Search Report for PCT/KR2013/000057 dated Apr. 29, 2013.
Intellectual Property Office of the Philippines Bureau of Patents, communication dated Aug. 9, 2016 in counterpart PH application No. 1-2014-501545.

* cited by examiner

Levocetirizine layer

Montelukast layer

STABLE PHARMACEUTICAL FORMULATION FOR ORAL ADMINISTRATION COMPRISING LEVOCETIRIZINE OR A PHARMACEUTICALLY ACCEPTABLE SALT THEREOF, AND MONTELUKAST OR A PHARMACEUTICALLY ACCEPTABLE SALT THEREOF

CROSS REFERENCE TO RELATED APPLICATIONS

This application is a National Stage of International Application No. PCT/KR2013/000057 filed Jan. 4, 2013, claiming priority based on Korean Patent Application No. 10-2012-0001954, filed Jan. 6, 2012, the contents of all of which are incorporated herein by reference in their entirety.

FIELD OF THE INVENTION

The present invention relates to a pharmaceutical formulation for oral administration for preventing or treating allergic rhinitis or asthma, which comprises (a) a first particle part comprising levocetirizine or a pharmaceutically acceptable salt thereof and an organic acid; and (b) a second particle part comprising montelukast or a pharmaceutically acceptable salt thereof.

BACKGROUND OF THE INVENTION

"Allergic rhinitis" refers to a symptomatic disorder of the nose induced by an IgE-mediated inflammation after allergen exposure of the membrane of the nose. The allergic rhinitis includes such symptoms as rhinorrhea, nasal obstruction, nasal itching, sneezing, ocular pruritis and so on.

"Asthma" refers to a disorder wherein inflammation of the airways causes bronchial mucosa to swell and muscular convulsion to occur in bronchi which restricts airflow into and out of the lungs. Asthma may cause such symptoms as shortness of breath, severe coughing, and in severe cases, status asthmaticus, which may result in even death.

Allergic rhinitis and asthma may develop separately; however, there is a study showing that approximately 58% of patients with allergic rhinitis have asthma as well and that 85~95% of patients with asthma also suffer from allergic rhinitis, indicating high rates of complications between said two patient groups. Thus, there has been a need for developing a combination composition, which has an improved stability and efficacy for treatment of said two conditions.

Meanwhile, Cetirizine is (2-(4-((4-chlorophenyl)phenylmethyl)-1-piperazinyl)ethoxy)acetic acid, and its levorotatory and dextrorotatory enantiomers were disclosed as "Levocetirizine" and "Dextrocetirizine", respectively.

Levocetirizine can be obtained by separation from a racemic mixture of Cetirizine or asymmetric synthesis, e.g., conventional methods disclosed in UK Patent No. 2225321, or enzymatic biocatalytic hydrolysis disclosed in U.S. Pat. Nos. 4,800,162 and 5,057,427. Levocetirizine possesses antihistamine properties and hence is useful as an antiallergenic and an antihistamine agent, as well as an anticonvulsant and a bronchodilator. Also, levocetirizine dihydrochloride is approved for treating allergic rhinitis and sold under Xyzal (Yuhan Corporation).

Montelukast is an antagonist inhibiting cysteinyl leukotriene type 1 (CysLT1) receptor, which is used for prevention and treatment of leukotriene-mediated diseases. Particularly, it has been reported that montelukast is effective in the treatment of allergic rhinitis, atopic dermatitis, chronic urticaria, sinusitis, nasal polyp, chronic obstructive pulmonary disease, conjunctivitis including nasal conjunctivitis, migraine, cystic fibrosis, viral bronchiolitis, and the like [see, e.g., S. E. Dahlen, *Eur. J. Pharmacol.*, 533(1-3), 40-56(2006)]. Further, Singulair (MSD) comprising montelukast sodium is approved for treating asthma in adults and pediatric patients of 2 years plus, and currently available in the market.

There has been a report relating to a pharmaceutical composition in a bilayer tablet form comprising montelukast sodium, which is stable in a basic condition, and levocetirizine dihydrochloride, which is stable in an acidic condition [R. T. Rathod, *J. Indian Med. Assoc.*, 107(8), 562-564 (2009)]. In the preparation of said composition in a tablet form, it is very difficult to completely separate montelukast and levocetirizine from each other. Even in case a bilayer tablet is formed, it is impossible to mechanically separate each active ingredient completely. Moreover, a bilayer tablet machine is required in order to manufacture such tablets.

In addition, Levocetirizine is also unstable in terms of physiochemical properties, and it is difficult to prepare a stable product against aging. There are three major degradation products of Levocetirizine, which include related substance A of formula (I), related substance B of formula (II), and related substance F of formula (III). Related substances A and B are produced via hydrolysis of Levocetirizine, and related substance F is created via side reaction of Levocetirizine with excipients or releasing agents of hard capsule. In fact, Levocetirizine shows an increased rate of formation of related substances A, B, and F under accelerated storage conditions, and hence it is not easy to provide stability during the manufacturing process of capsule formulation.

Formula (I)

Formula (II)

Formula (III)

Montelukast is known to be unstable when exposed to light, heat, or moisture, and yields such degraded products as montelukast sulfoxide of formula (IV) and montelukast cis-isomer of formula (V). According to a reference [see M. M. Al Omani et al., *J. Pharm. and Biomed. Anal.*, 45, 465-471(2007)], when a commercially available Singulair chewable tablet was exposed to sunlight, the amount of montelukast sulfoxide was increased by 2.4% after 3 weeks; and when montelukast in 0.1 M hydrochloric acid solution was exposed to sodium light for 6 hours, the amount of montelukast cis-isomer was increased by 14.6%. As shown in the report, it is not easy to prepare a stable montelukast product against aging.

Formula (IV)

Formula (V)

During the manufacturing process of hard capsule, capsule materials and excipients are employed so as to maintain the capsule shape and make the capsule surface smooth. Examples of capsule materials include gelatin, pullulan, hypromellose, polyvinyl alcohol and the like; and examples of excipients include diacetylated monoglyceride, sucrose fatty acid ester, sodium lauryl sulfate and the like. Also, a release agent such as mineral oil, lecithin and the like is used for release of capsules easily from the mold which forms the shape of the capsule.

The present inventors have conducted a research on a combination formulation comprising levocetirizine or a pharmaceutically acceptable salt thereof and montelukast or a pharmaceutically acceptable salt thereof as active ingredients. They have discovered that when levocetirizine and montelukast were prepared in separate tablets and then filled in a hard capsule, the amount of related substances increased more rapidly as compared to the composition in the form of single-active ingredient tablets due to materials derived from excipients and release agents as well as the moisture content existing in the capsule, and hence stability of active ingredients is deteriorated. Therefore, the present inventors have endeavored to resolve the problem and have found that the production of levocetirizine and montelukast related substances can be effectively inhibited when an organic acid such as citric acid is employed in a particle part comprising levocetirizine, and thus, have good long-term storage stability, even after the active ingredients were filled in a hard capsule.

SUMMARY OF THE INVENTION

Therefore, it is an object of the present invention to provide a pharmaceutical formulation for oral administration comprising levocetirizine or a pharmaceutically acceptable salt thereof, and montelukast or a pharmaceutically acceptable salt thereof, wherein the active ingredients are charged in a hard capsule for good long-term storage stability, for prevention or treatment of allergic rhinitis or asthma.

It is another object of the present invention to provide a method for preparing the above pharmaceutical formulation for oral administration.

In accordance with the object of the present invention, there is provided a pharmaceutical formulation for oral administration for preventing or treating allergic rhinitis or asthma, which comprises:

(a) a first particle part comprising levocetirizine or a pharmaceutically acceptable salt thereof and an organic acid; and (b) a second particle part comprising montelukast or a pharmaceutically acceptable salt thereof.

In accordance with another object of the present invention, there is provided a method for preparing the pharmaceutical formulation, which comprises the steps of:

(i) mixing levocetirizine or a pharmaceutically acceptable salt thereof, a pharmaceutically acceptable additive and an organic acid, and tableting the mixture, wherein the organic acid is employed in an amount of 40 to 1000 parts by weight, based on 100 parts of levocetirizine;

(ii) mixing montelukast or a pharmaceutically acceptable salt thereof and a pharmaceutically acceptable additive, and tableting the mixture; and (iii) filling the levocetirizine tablet obtained in step (i) and the montelukast tablet obtained in step (ii) into a hard capsule.

In accordance with a further object of the present invention, there is provided a capsule formulation prepared by the method above.

BRIEF DESCRIPTION OF THE DRAWING

The above and other objects and features of the present invention will become apparent from the following descriptions of the invention, when taken in conjunction with the accompanying drawings.

DETAILED DESCRIPTION OF THE INVENTION

Hereinafter, the present invention is explained in detail.

The present invention provides a pharmaceutical formulation for preventing or treating allergic rhinitis or asthma, which comprises (a) a first particle part comprising levocetirizine or a pharmaceutically acceptable salt thereof and an organic acid; and (b) a second particle part comprising montelukast or a pharmaceutically acceptable salt thereof.

The pharmaceutical formulation of the present invention employs an antihistamine agent, levocetirizine, as a first active ingredient to reduce early allergic rhinitis and asthma reaction, as well as an anti-leukotriene agent, montelukast, as a second active ingredient to treat and prevent one of the major symptoms of late allergic rhinitis, i.e. nasal obstruction and asthma.

Levocetirizine or the pharmaceutically acceptable salt thereof comprised in the first particle part in the present invention is, for example, disclosed in European Patent Application Nos. 0058146, 0601028 and 0801064, UK Patent Nos. 2225320 and 2225321, U.S. Pat. No. 5,478,941, and International Patent Publication No. WO 97/37982. The pharmaceutically acceptable salt of levocetirizine may include, but not limited to, an acid-addition salt of the pharmaceutically acceptable non-toxic organic or inorganic acid, such as salts of acetic acid, citric acid, maleic acid, succinic acid, ascorbic acid, hydrochloric acid, hydrobromic acid, sulfuric acid, phosphoric acid and the like; a metal salt (e.g., sodium salt or potassium salt), ammonium salt, amine salt, and amino acid salt, preferably levocetirizine dihydrochloride salt. The daily dosage amount of levocetirizine or the pharmaceutically acceptable salt thereof is 0.4 to 100 mg, preferably 1 to 50 mg, more preferably 2.5 to 20 mg per unit dosage form.

Montelukast or the pharmaceutically acceptable salt thereof comprised in the second particle part in the present invention is preferably montelukast sodium. The daily dosage amount of montelukast or the pharmaceutically acceptable salt thereof is 0.4 to 100 mg, preferably 1 to 50 mg, more preferably 2.5 to 20 mg per unit dosage form.

The pharmaceutical formulation of the present invention comprises an organic acid, as a stabilizing agent, in an amount of 40 to 1000 parts by weight, preferably 50 to 500 parts by weight, based on 100 parts of levocetirizine.

The organic acid may reduce the production of levocetirizine related substances and montelukast related substances produced due to an excipient and a release agent of a capsule. If the amount of the organic acid is less than 40 parts by weight, the effect on the stabilities of levocetirizine and montelukast becomes insignificant; meanwhile, the amount exceeding 1000 parts by weight of the organic acid could cause an irritation when administered to the body and unnecessary organic acid can be absorbed into the body system.

Examples of the organic acid may be selected from the group consisting of citric acid, tartaric acid, succinic acid, glutamic acid, aspartic acid, oxalic acid, malic acid, acetic acid, sorbic acid, ascorbic acid, alginic acid, fumaric acid, lactic acid and a mixture thereof.

The pharmaceutical formulation of the present invention may be prepared in the form of an oral solid pharmaceutical formulation selected from the group consisting of powder, granule, pellet, tablet and capsule, preferably in the form of a capsule.

In one embodiment of the present invention, the pharmaceutical formulation of the present invention is a capsule formulation which comprises (a) a first particle part comprising levocetirizine or a pharmaceutically acceptable salt thereof and an organic acid; and (b) a second particle part comprising montelukast or a pharmaceutically acceptable salt thereof, wherein said particle parts are filled physically separated and in a capsule.

The first or second particle part may be in the form of a tablet, preferably in the form of a mini tablet.

The first or second particle part may each further comprise a pharmaceutically acceptable additive. The pharmaceutically acceptable additive may be selected from the group consisting of a diluent, a disintegrant, a binder, a lubricant, and a mixture thereof.

Suitable examples of the diluent may include microcrystalline cellulose, lactose, ludipress, mannitol, calcium phosphate monobasic, starch, low-substituted hydroxypropylcellulose, and a mixture thereof. The diluent may be used in an amount ranging from 1 to 99% by weight, preferably 5 to 95% by weight based on the total weight of the tablet.

Examples of the disintegrant may include any material showing a stable disintegration in a liquid environment, which is selected from the group consisting of crospovidone, sodium starch glycolate, croscarmellose sodium, low-substituted hydroxypropylcellulose, starch, alginate or a sodium salt thereof, and a mixture thereof. Preferably, the disintegrant may be crospovidone, sodium starch glycolate, croscarmellose sodium, low-substituted hydroxypropylcellulose or a mixture thereof. The disintegrant may be used in an amount ranging from 1 to 30% by weight, preferably 2 to 20% by weight based on the total weight of the tablet.

Examples of the binder may include hydroxypropylcellulose, hypromellose, polyvinylpyrrolidone, copovidone, macrogol, light anhydrous silicic acid, synthetic aluminum silicate, silicate derivatives such as calcium silicate or magnesium metasilicate aluminate, phosphate salts such as calcium phosphate dibasic, carbonate salts such as calcium carbonate, and a mixture thereof. The binder may be used in an amount ranging from 1 to 30% by weight, preferably 2 to 20% by weight based on the total weight of the tablet.

Examples of the lubricant may include stearic acid, metal salts of stearic acid such as calcium stearate or magnesium stearate, talc, colloid silica, sucrose fatty acid ester, hydrogenated vegetable oil, high melting point wax, glyceryl fatty acid ester, glycerol dibehenate and a mixture thereof. The lubricant may be used in an amount ranging from 0.3 to 5% by weight, preferably 0.5 to 3% by weight based on the total weight of the tablet.

Further, each tablet comprising the first or second particle part may further comprise a coating layer. The coating layer may be formed on the surface of at least one selected from said tablets so as to completely separate montelukast and levocetirizine.

In the present invention, the coating substrate used for the coating layer may be conventional high molecular compounds. Examples of the coating substrate may include hypromellose, hydroxypropylcellulose, methylcellulose, ethylcellulose, polyvinyl alcohol, polyvinylpyrrolidone, hydroxyethylcellulose, but not limited thereto. The amount of the coating substrate is preferably kept at minimum so as to improve efficiency in production and provide the formulation of an optimal size for administration. Therefore, the coating substrate may be used in an amount ranging from 0.5 to 20% by weight, preferably 1 to 10% by weight based on the total weight of the tablet.

In the capsule formulation of the present invention, the capsule may be any conventional hard capsules that are generally used in the preparation of medicine. The hard capsule substrates used in the present invention may be selected from the group consisting of gelatin, pullulan (NP caps™, etc; Capsugel), hypromellose and polyvinyl alcohol.

In the present invention, the hard capsules may have any conventional capsule size used in the preparation of medicine. The internal volume of hard capsules varies with the size thereof: No. 00 (0.95 mL), No. 0 (0.68 mL), No. 1 (0.47 mL), No. 2 (0.37 mL), No. 3 (0.27 mL) and No. 4 (0.20 mL) (Suheung Capsule Co, Korea). The size of the capsule is preferably small for patients' convenience; however, due to mass limit of the contents to be filled in the capsule, the size of the capsule used in the present invention may include No. 0, No. 1, No. 2, No. 3, and No. 4, preferably No. 1, No. 2, and No. 3.

The pharmaceutical formulation of the present invention may be used for preventing or treating allergic rhinitis or asthma, and the allergic rhinitis may be selected from the group consisting of symptoms such as rhinorrhea, nasal obstruction, nasal itching, sneezing and ocular pruritis.

Further, the present invention provides a method for preparing the pharmaceutical formulation, which comprises the steps of: (i) mixing levocetirizine or a pharmaceutically acceptable salt thereof, a pharmaceutically acceptable additive and an organic acid and tableting the mixture, wherein the organic acid is employed in an amount of 40 to 1000 parts by weight, based on 100 parts of levocetirizine; (ii) mixing montelukast or a pharmaceutically acceptable salt thereof and a pharmaceutically acceptable additive and tableting the mixture; and (iii) filling the levocetirizine tablet obtained in step (i) and the montelukast tablet obtained in step (ii) into a hard capsule.

The method may further comprise a step of coating the tablet produced in step (i) or (ii). The capsule formulation prepared in the present invention may be administered by oral route and the like.

Further, the present invention provides a capsule formulation prepared by the method above.

The capsule formulation of the present invention comprises montelukast and levocetirizine physically separately in the hard capsule, and thus completely separate said two active ingredients. Therefore, the reactivity between two active ingredients can be minimized and the stability of the formulation is enhanced, thus optimizing therapeutic efficacy. It is also advantageous because preexisting analytical method for the evaluation of time-dependent stability of a single formulation can be also used for the inventive formulation, instead of developing a new analytical method. In addition, the organic acid comprised in the first particle part can not only enhance stability of levocetirizine, but also stabilize montelukast.

The following Examples are intended to further illustrate the present invention without limiting its scope.

EXAMPLE 1

Preparation of Combination Formulation I

| Levocetirizine Layer | Quantity |
| --- | --- |
| Levocetirizine dihydrochloride | 5.0 mg |
| Ludipress | 60.5 mg |
| Microcrystalline cellulose | 25.0 mg |
| Citric acid | 5.0 mg |
| Croscarmellose sodium | 3.0 mg |
| Light anhydrous silicic acid | 0.5 mg |
| Magnesium stearate | 1.0 mg |
| Opadry white (Y-1-7000) | 3.0 mg |
| Distilled water | (15.0 mg) |

| Montelukast Layer | Quantity |
| --- | --- |
| Montelukast sodium | 10.4 mg (Montelukast, 10 mg) |
| D-mannitol | 74.3 mg |
| Microcrystalline cellulose | 74.3 mg |
| Light anhydrous silicic acid | 5.0 mg |
| Hydroxypropylcellulose | 4.0 mg |
| Sodium starch glycolate | 30.0 mg |
| Magnesium stearate | 2.0 mg |
| Hypromellose | 1.73 mg |
| Hydroxypropylcellulose | 1.73 mg |
| Titanium dioxide | 1.5 mg |
| Yellow iron oxide | 0.036 mg |
| Red iron oxide | 0.004 mg |
| Distilled water | (50.0 mg) |

Levocetirizine dihydrochloride, ludipress (BASF), microcrystalline cellulose, citric acid, croscarmellose sodium, light anhydrous silicic acid and magnesium stearate were passed through a sieve and mixed, and the mixture was pressed to a tablet using a round punch having a diameter of 5.5 mm to obtain a levocetirizine tablet. Then, the levocetirizine tablet was coated with a coating solution prepared by dissolving Opadry White (Y-1-7000, Colorcon) in distilled water.

Meanwhile, montelukast sodium, D-mannitol, microcrystalline cellulose, light anhydrous silicic acid, hydroxypropylcellulose, sodium starch glycolate and magnesium stearate were passed through a sieve and mixed, and the mixture was pressed to a tablet using a round punch having a diameter of 5.5 mm to obtain a montelukast tablet. Then, the montelukast tablet was coated with a coating solution prepared by dissolving hypromellose, hydroxypropylcellulose, titanium dioxide, yellow iron oxide, red iron oxide in distilled water.

Finally, said two tablets thus obtained were filled into a No. 1 hard capsule which is mainly composed of gelatin, to obtain a capsule formulation comprising 10 mg of montelukast and 5 mg of levocetirizine.

EXAMPLE 2

Preparation of Combination Formulation II

The procedure of Example 1 was repeated except for using a hard capsule which is mainly composed of pullulan, to obtain a capsule formulation comprising 10 mg of montelukast and 5 mg of levocetirizine.

EXAMPLE 3

Preparation of Combination Formulation III

The procedure of Example 1 was repeated except for using a hard capsule which is mainly composed of hypromellose, to obtain a capsule formulation comprising 10 mg of montelukast and 5 mg of levocetirizine.

EXAMPLE 4

Preparation of Combination Formulation IV

| Levocetirizine Layer | Quantity |
|---|---|
| Levocetirizine dihydrochloride | 5.0 mg |
| Ludipress | 60.5 mg |
| Microcrystalline cellulose | 25.0 mg |
| Tartaric acid | 5.0 mg |
| Croscarmellose sodium | 3.0 mg |
| Light anhydrous silicic acid | 0.5 mg |
| Magnesium stearate | 1.0 mg |
| Opadry white (Y-1-7000) | 3.0 mg |
| Distilled water | (15.0 mg) |

| Montelukast Layer | Quantity |
|---|---|
| Montelukast sodium | 10.4 mg (Montelukast, 10 mg) |
| D-mannitol | 74.3 mg |
| Microcrystalline cellulose | 74.3 mg |
| Light anhydrous silicic acid | 5.0 mg |
| Hydroxypropylcellulose | 4.0 mg |
| Sodium starch glycolate | 30.0 mg |
| Magnesium stearate | 2.0 mg |
| Hypromellose | 1.73 mg |
| Hydroxypropylcellulose | 1.73 mg |
| Titanium dioxide | 1.5 mg |
| Yellow iron oxide | 0.036 mg |
| Red iron oxide | 0.004 mg |
| Distilled water | (50.0 mg) |

Levocetirizine dihydrochloride, ludipress, microcrystalline cellulose, tartaric acid, croscarmellose sodium, light anhydrous silicic acid and magnesium stearate were passed through a sieve and mixed, and the mixture was pressed to a tablet using a round punch having a diameter of 5.5 mm to obtain a levocetirizine tablet. Then, the levocetirizine tablet was coated with a coating solution prepared by dissolving Opadry White (Y-1-7000) in distilled water.

Meanwhile, montelukast sodium, D-mannitol, microcrystalline cellulose, light anhydrous silicic acid, hydroxypropylcellulose, sodium starch glycolate and magnesium stearate were passed through a sieve and mixed, and the mixture was pressed to a tablet using a round punch having a diameter of 5.5 mm to obtain a montelukast tablet. Then, the montelukast tablet was coated with a coating solution prepared by dissolving hypromellose, hydroxypropylcellulose, titanium dioxide, yellow iron oxide and red iron oxide in distilled water.

Finally, said two tablets thus obtained were filled into a No. 1 hard capsule which is mainly composed of gelatin, to obtain a capsule formulation comprising 10 mg of montelukast and 5 mg of levocetirizine.

EXAMPLE 5

Preparation of Combination Formulation V

| Levocetirizine Layer | Quantity |
|---|---|
| Levocetirizine dihydrochloride | 5.0 mg |
| Ludipress | 60.5 mg |
| Microcrystalline cellulose | 25.0 mg |
| Succinic acid | 5.0 mg |
| Croscarmellose sodium | 3.0 mg |
| Light anhydrous silicic acid | 0.5 mg |
| Magnesium stearate | 1.0 mg |
| Opadry white (Y-1-7000) | 3.0 mg |
| Distilled water | (15.0 mg) |

| Montelukast Layer | Quantity |
|---|---|
| Montelukast sodium | 10.4 mg (Montelukast, 10 mg) |
| D-mannitol | 74.3 mg |
| Microcrystalline cellulose | 74.3 mg |
| Light anhydrous silicic acid | 5.0 mg |
| Hydroxypropylcellulose | 4.0 mg |
| Sodium starch glycolate | 30.0 mg |
| Magnesium stearate | 2.0 mg |
| Hypromellose | 1.73 mg |
| Hydroxypropylcellulose | 1.73 mg |
| Titanium dioxide | 1.5 mg |
| Yellow iron oxide | 0.036 mg |
| Red iron oxide | 0.004 mg |
| Distilled water | (50.0 mg) |

Levocetirizine dihydrochloride, ludipress, microcrystalline cellulose, succinic acid, croscarmellose sodium, light anhydrous silicic acid and magnesium stearate were passed through a sieve and mixed, and the mixture was pressed to a tablet using a round punch having a diameter of 5.5 mm to obtain a levocetirizine tablet. Then, the levocetirizine tablet was coated with a coating solution prepared by dissolving Opadry White (Y-1-7000) in distilled water.

Meanwhile, montelukast sodium, D-mannitol, microcrystalline cellulose, light anhydrous silicic acid, hydroxypropylcellulose, sodium starch glycolate and magnesium stearate were passed through a sieve and mixed, and pressed to a tablet using a round punch having a diameter of 5.5 mm to obtain a montelukast tablet. Then, the montelukast tablet was coated with a coating solution prepared by dissolving hypromellose, hydroxypropylcellulose, titanium dioxide, yellow iron oxide and red iron oxide in distilled water.

Finally, said two tablets thus obtained were filled into a No. 1 hard capsule which is mainly composed of gelatin, to obtain a capsule formulation comprising 10 mg of montelukast and 5 mg of levocetirizine.

EXAMPLE 6

Preparation of Combination Formulation VI

| Levocetirizine Layer | Quantity |
|---|---|
| Levocetirizine dihydrochloride | 5.0 mg |
| Ludipress | 60.5 mg |
| Microcrystalline cellulose | 25.0 mg |
| Ascorbic acid | 5.0 mg |
| Croscarmellose sodium | 3.0 mg |
| Light anhydrous silicic acid | 0.5 mg |

-continued

| Levocetirizine Layer | Quantity |
|---|---|
| Magnesium stearate | 1.0 mg |
| Opadry white (Y-1-7000) | 3.0 mg |
| Distilled water | (15.0 mg) |

| Montelukast Layer | Quantity |
|---|---|
| Montelukast sodium | 10.4 mg (Montelukast, 10 mg) |
| D-mannitol | 74.3 mg |
| Microcrystalline cellulose | 74.3 mg |
| Light anhydrous silicic acid | 5.0 mg |
| Hydroxypropylcellulose | 4.0 mg |
| Sodium starch glycolate | 30.0 mg |
| Magnesium stearate | 2.0 mg |
| Hypromellose | 1.73 mg |
| Hydroxypropylcellulose | 1.73 mg |
| Titanium dioxide | 1.5 mg |
| Yellow iron oxide | 0.036 mg |
| Red iron oxide | 0.004 mg |
| Distilled water | (50.0 mg) |

Levocetirizine dihydrochloride, ludipress, microcrystalline cellulose, ascorbic acid, croscarmellose sodium, light anhydrous silicic acid and magnesium stearate were passed through a sieve and mixed, and the mixture was pressed to a tablet using a round punch having a diameter of 5.5 mm to obtain a levocetirizine tablet. Then, the levocetirizine tablet was coated with a coating solution prepared by dissolving Opadry White (Y-1-7000) in distilled water.

Meanwhile, montelukast sodium, D-mannitol, microcrystalline cellulose, light anhydrous silicic acid, hydroxypropylcellulose, sodium starch glycolate and magnesium stearate were passed through a sieve and mixed, and pressed to a tablet using a round punch having a diameter of 5.5 mm to obtain a montelukast tablet. Then, the montelukast tablet was coated with a coating solution prepared by dissolving hypromellose, hydroxypropylcellulose, titanium dioxide, yellow iron oxide and red iron oxide in distilled water.

Finally, said two tablets thus obtained were filled into a No. 1 hard capsule which is mainly composed of gelatin, to obtain a capsule formulation comprising 10 mg of montelukast and 5 mg of levocetirizine.

COMPARATIVE EXAMPLE 1

Preparation of Combination Formulation VII

| Levocetirizine Layer | Quantity |
|---|---|
| Levocetirizine dihydrochloride | 5.0 mg |
| Ludipress | 60.5 mg |
| Microcrystalline cellulose | 30.0 mg |
| Croscarmellose sodium | 3.0 mg |
| Light anhydrous silicic acid | 0.5 mg |
| Magnesium stearate | 1.0 mg |
| Opadry white (Y-1-7000) | 3.0 mg |
| Distilled water | (15.0 mg) |

| Montelukast Layer | Quantity |
|---|---|
| Montelukast sodium | 10.4 mg (Montelukast, 10 mg) |
| D-mannitol | 74.3 mg |

| Montelukast Layer | Quantity |
|---|---|
| Microcrystalline cellulose | 74.3 mg |
| Light anhydrous silicic acid | 5.0 mg |
| Hydroxypropylcellulose | 4.0 mg |
| Sodium starch glycolate | 30.0 mg |
| Magnesium stearate | 2.0 mg |
| Hypromellose | 1.73 mg |
| Hydroxypropylcellulose | 1.73 mg |
| Titanium dioxide | 1.5 mg |
| Yellow iron oxide | 0.036 mg |
| Red iron oxide | 0.004 mg |
| Distilled water | (50.0 mg) |

Levocetirizine dihydrochloride, ludipress, microcrystalline cellulose, croscarmellose sodium, light anhydrous silicic acid and magnesium stearate were passed through a sieve and mixed, and the mixture pressed to a tablet using a round punch having a diameter of 5.5 mm to obtain a levocetirizine tablet. Then, the levocetirizine tablet was coated with a coating solution prepared by dissolving Opadry White (Y-1-7000) in distilled water.

Meanwhile, montelukast sodium, D-mannitol, microcrystalline cellulose, light anhydrous silicic acid, hydroxypropylcellulose, sodium starch glycolate and magnesium stearate were passed through a sieve and mixed, and the mixture was pressed to a tablet using a round punch having a diameter of 5.5 mm to obtain a montelukast tablet. Then, the montelukast tablet was coated with a coating solution prepared by dissolving hypromellose, hydroxypropylcellulose, titanium dioxide, yellow iron oxide and red iron oxide in distilled water.

Finally, said two tablets thus obtained were filled into a No. 1 hard capsule which is mainly composed of gelatin, to obtain a capsule formulation comprising 10 mg of montelukast and 5 mg of levocetirizine.

COMPARATIVE EXAMPLE 2

Preparation of Combination Formulation VIII

The procedure of Comparative Example 1 was repeated except for using a hard capsule which is mainly composed of pullulan, to obtain a capsule formulation comprising 10 mg of montelukast and 5 mg of levocetirizine.

COMPARATIVE EXAMPLE 3

Preparation of Combination Formulation IX

The procedure of Comparative Example 1 was repeated except for using a hard capsule which is mainly composed of hypromellose, to obtain a capsule formulation comprising 10 mg of montelukast and 5 mg of levocetirizine.

COMPARATIVE EXAMPLE 4

Preparation of Combination Formulation X

| Levocetirizine Layer | Quantity |
|---|---|
| Levocetirizine dihydrochloride | 5.0 mg |
| Ludipress | 60.5 mg |
| Microcrystalline cellulose | 25.0 mg |
| Phosphoric acid | 5.0 mg |

-continued

| Levocetirizine Layer | Quantity |
|---|---|
| Croscarmellose sodium | 3.0 mg |
| Light anhydrous silicic acid | 0.5 mg |
| Magnesium stearate | 1.0 mg |
| Opadry white (Y-1-7000) | 3.0 mg |
| Distilled water | (15.0 mg) |

| Montelukast Layer | Quantity |
|---|---|
| Montelukast sodium | 10.4 mg (Montelukast, 10 mg) |
| D-mannitol | 74.3 mg |
| Microcrystalline cellulose | 74.3 mg |
| Light anhydrous silicic acid | 5.0 mg |
| Hydroxypropylcellulose | 4.0 mg |
| Sodium starch glycolate | 30.0 mg |
| Magnesium stearate | 2.0 mg |
| Hypromellose | 1.73 mg |
| Hydroxypropylcellulose | 1.73 mg |
| Titanium dioxide | 1.5 mg |
| Yellow iron oxide | 0.036 mg |
| Red iron oxide | 0.004 mg |
| Distilled water | (50.0 mg) |

Levocetirizine dihydrochloride, ludipress, microcrystalline cellulose, croscarmellose sodium, light anhydrous silicic acid and magnesium stearate were passed through a sieve and mixed, and added with phosphoric acid, and the mixture was pressed to a tablet using a round punch having a diameter of 5.5 mm to obtain a levocetirizine tablet. Then, the levocetirizine tablet was coated with a coating solution prepared by dissolving Opadry White (Y-1-7000) in distilled water.

Meanwhile, montelukast sodium, D-mannitol, microcrystalline cellulose, light anhydrous silicic acid, hydroxypropylcellulose, sodium starch glycolate and magnesium stearate were passed through a sieve and mixed, and the mixture was pressed to a tablet using a round punch having a diameter of 5.5 mm to obtain a montelukast tablet. Then, the montelukast tablet was coated with a coating solution prepared by dissolving hypromellose, hydroxypropylcellulose, titanium dioxide, yellow iron oxide and red iron oxide in distilled water.

Finally, said two tablets thus obtained were filled into a No. 1 hard capsule which is mainly composed of gelatin, to obtain a capsule formulation comprising 10 mg of montelukast and 5 mg of levocetirizine.

COMPARATIVE EXAMPLE 5

Preparation of Combination Formulation XI

| Levocetirizine Layer | Quantity |
|---|---|
| Levocetirizine dihydrochloride | 5.0 mg |
| Ludipress | 60.5 mg |
| Microcrystalline cellulose | 25.0 mg |
| Sodium hydroxide | 5.0 mg |
| Croscarmellose sodium | 3.0 mg |
| Light anhydrous silicic acid | 0.5 mg |
| Magnesium stearate | 1.0 mg |
| Opadry white (Y-1-7000) | 3.0 mg |
| Distilled water | (15.0 mg) |

| Montelukast Layer | Quantity |
|---|---|
| Montelukast sodium | 10.4 mg (Montelukast, 10 mg) |
| D-mannitol | 74.3 mg |
| Microcrystalline cellulose | 74.3 mg |
| Light anhydrous silicic acid | 5.0 mg |
| Hydroxypropyl cellulose | 4.0 mg |
| Sodium starch glycolate | 30.0 mg |
| Magnesium stearate | 2.0 mg |
| Hypromellose | 1.73 mg |
| Hydroxypropyl cellulose | 1.73 mg |
| Titanium dioxide | 1.5 mg |
| Yellow iron oxide | 0.036 mg |
| Red iron oxide | 0.004 mg |
| Distilled water | (50.0 mg) |

Levocetirizine dihydrochloride, ludipress, microcrystalline cellulose, sodium hydroxide, croscarmellose sodium, light anhydrous silicic acid and magnesium stearate were passed through a sieve and mixed, and the mixture was pressed to a tablet using a round punch having a diameter of 5.5 mm to obtain a levocetirizine tablet. Then, the levocetirizine tablet was coated with a coating solution prepared by dissolving Opadry White (Y-1-7000) in distilled water.

Meanwhile, montelukast sodium, D-mannitol, microcrystalline cellulose, light anhydrous silicic acid, hydroxypropylcellulose, sodium starch glycolate and magnesium stearate were passed through a sieve and mixed, and the mixture was pressed to a tablet using a round punch having a diameter of 5.5 mm to obtain a montelukast tablet. Then, the montelukast tablet was coated with a coating solution prepared by dissolving hypromellose, hydroxypropylcellulose, titanium dioxide, yellow iron oxide and red iron oxide in distilled water.

Finally, said two tablets thus obtained were filled into a No. 1 hard capsule which is mainly composed of gelatin, to obtain a capsule formulation comprising 10 mg of montelukast and 5 mg of levocetirizine.

COMPARATIVE EXAMPLE 6

Preparation of Levocetirizine Tablet (Single Tablet)

|  | Quantity |
|---|---|
| Levocetirizine dihydrochloride | 5.0 mg |
| Ludipress | 60.5 mg |
| Microcrystalline cellulose | 30.0 mg |
| Croscarmellose sodium | 3.0 mg |
| Light anhydrous silicic acid | 0.5 mg |
| Magnesium stearate | 1.0 mg |
| Opadry white (Y-1-7000) | 3.0 mg |
| Distilled water | (15.0 mg) |

Levocetirizine dihydrochloride, ludipress, microcrystalline cellulose, croscarmellose sodium, light anhydrous silicic acid and magnesium stearate were passed through a sieve and mixed, and the mixture was pressed to a tablet using a round punch having a diameter of 5.5 mm to obtain a levocetirizine tablet. Then, the levocetirizine tablet was coated with a coating solution prepared by dissolving Opadry White (Y-1-7000) in distilled water.

EXPERIMENTAL EXAMPLE 1

Stability Test Under Accelerated Conditions

The combination capsule formulations comprising levocetirizine and montelukast prepared in Examples 1 to 6 and Comparative Examples 1 to 5, and the levocetirizine single tablet prepared in Comparative Example 6 were stored under the following accelerated storage conditions. The amount of levocetirizine and montelukast related substances (impurities) were measured so as to compare the stability of the formulations. The results are shown in Tables 3 and 4, and FIGS. 1 and 2.

<Accelerated Storage Conditions>

Storage conditions: contained in an HDPE bottle at 40° C., 75% RH

Test duration: Initial and 6 months

Analysis target: levocetirizine and levocetirizine related substances, and montelukast and montelukast related substances.

<Analysis Conditions of Levocetirizine and its Related Substances>

Column: Symmetry Shield RP18 column for HPLC (Waters) having a stainless pipe (inner diameter of 4.6 mm×length of 25 cm) filled with octadecylsilyl silica gel (particle size: 5 μm)

Eluents: A—Distilled water (DW):Acetonitrile:10% Trifluoroacetic acid (TFA)=69:30:1 (v/v/v)

B—DW:Acetonitrile:10% TFA=29:70:1 (v/v/v)

TABLE 1

| Elution Conditions | | |
|---|---|---|
| Time (min) | A (%) | B (%) |
| 0 | 100 | 0 |
| 2 | 100 | 0 |
| 30 | 25 | 75 |

TABLE 1-continued

| Elution Conditions | | |
|---|---|---|
| Time (min) | A (%) | B (%) |
| 40 | 100 | 0 |
| 50 | 100 | 0 |

Detector: UV-absorption detector (absorbance at 230 nm)
Flow rate: 1.2 mL/min
Column temperature: 30° C.

<Analysis Conditions of Montelukast and its Related Substances>

Column: Zorbax SB-Phenyl column for HPLC (Agilent Zorbax) having a stainless pipe (inner diameter of 4.6 mm×length of 25 cm) filled with diisopropyl phenethyl silica gel (particle size: 5 μm)

Eluents: A—Distilled water containing 0.1% TFA

B—Acetonitrile containing 0.1% TFA

TABLE 2

| Elution Conditions | | |
|---|---|---|
| Time (min) | A (%) | B (%) |
| 0 | 60 | 40 |
| 20 | 10 | 90 |
| 30 | 10 | 90 |
| 31 | 60 | 40 |
| 35 | 60 | 40 |

Detector: UV-absorption detector (absorbance at 238 nm)
Flow rate: 1.5 mL/min
Column temperature: 25° C.

The content changes of levocetirizine related substances A, B and F are shown in Table 3, and the changes of montelukast related substances, i.e., montelukast sulfoxide and montelukast cis-isomer, are shown in Table 4.

TABLE 3

Changes of Levocetirizine related substances

| | Initial | | | | 6 months | | | |
|---|---|---|---|---|---|---|---|---|
| Sample | Rel. Sub. A (%) | Rel. Sub. B (%) | Rel. Sub. F (%) | Total Rel. Sub. (%) | Rel. Sub. A (%) | Rel. Sub. B (%) | Rel. Sub. F (%) | Total Rel. Sub. (%) |
| Ex. 1 | 0.01 | 0.02 | 0.00 | 0.08 | 0.04 | 0.04 | 0.02 | 0.14 |
| Ex. 2 | 0.01 | 0.01 | 0.00 | 0.06 | 0.03 | 0.03 | 0.01 | 0.11 |
| Ex. 3 | 0.01 | 0.01 | 0.00 | 0.06 | 0.03 | 0.03 | 0.01 | 0.10 |
| Ex. 4 | 0.01 | 0.02 | 0.00 | 0.07 | 0.04 | 0.05 | 0.03 | 0.18 |
| Ex. 5 | 0.01 | 0.02 | 0.00 | 0.08 | 0.04 | 0.04 | 0.03 | 0.17 |
| Ex. 6 | 0.01 | 0.02 | 0.00 | 0.08 | 0.04 | 0.04 | 0.03 | 0.17 |
| Comp. Ex. 1 | 0.01 | 0.02 | 0.00 | 0.12 | 0.32 | 0.31 | 0.35 | 1.13 |
| Comp. Ex. 2 | 0.01 | 0.02 | 0.00 | 0.08 | 0.22 | 0.19 | 0.26 | 0.86 |
| Comp. Ex. 3 | 0.01 | 0.02 | 0.00 | 0.08 | 0.15 | 0.13 | 0.15 | 0.62 |
| Comp. Ex. 4 | 0.01 | 0.02 | 0.00 | 0.09 | 0.27 | 0.29 | 0.23 | 0.93 |
| Comp. Ex. 5 | 0.01 | 0.02 | 0.00 | 0.09 | 0.56 | 0.62 | 0.52 | 2.13 |
| Comp. Ex. 6 | 0.01 | 0.02 | 0.00 | 0.08 | 0.04 | 0.04 | 0.00 | 0.12 |

TABLE 4

Changes of Montelukast related substances

| | Initial | | | 6 months | | |
|---|---|---|---|---|---|---|
| Sample | Montelukast sulfoxide (%) | Montelukast cis-isomer (%) | Total Rel. Sub. (%) | Montelukast sulfoxide (%) | Montelukast cis-isomer (%) | Total Rel. Sub. (%) |
| Ex. 1 | 0.08 | 0.03 | 0.15 | 0.15 | 0.06 | 0.28 |
| Ex. 2 | 0.09 | 0.03 | 0.16 | 0.12 | 0.05 | 0.23 |
| Ex. 3 | 0.08 | 0.03 | 0.15 | 0.10 | 0.04 | 0.19 |
| Ex. 4 | 0.08 | 0.03 | 0.16 | 0.15 | 0.06 | 0.30 |
| Ex. 5 | 0.08 | 0.03 | 0.16 | 0.16 | 0.07 | 0.31 |
| Ex. 6 | 0.09 | 0.03 | 0.15 | 0.17 | 0.06 | 0.33 |
| Comp. Ex. 1 | 0.08 | 0.04 | 0.16 | 0.33 | 0.12 | 0.65 |
| Comp. Ex. 2 | 0.08 | 0.03 | 0.15 | 0.25 | 0.09 | 0.55 |
| Comp. Ex. 3 | 0.08 | 0.03 | 0.15 | 0.26 | 0.08 | 0.52 |
| Comp. Ex. 4 | 0.08 | 0.03 | 0.15 | 0.34 | 0.13 | 0.67 |
| Comp. Ex. 5 | 0.08 | 0.03 | 0.15 | 0.14 | 0.06 | 0.25 |

Figure 1:
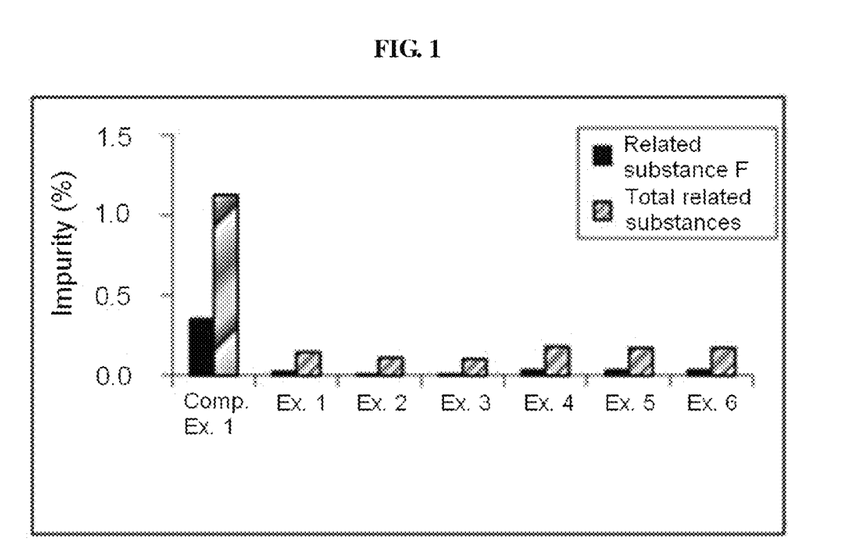
FIG. 1 shows the amount of levocetirizine related substances for the capsule formulations obtained in Examples 1 to 6 and Comparative Example 1 under accelerated storage condition (40° C./75% RH) for 6 months.
Figure 2:
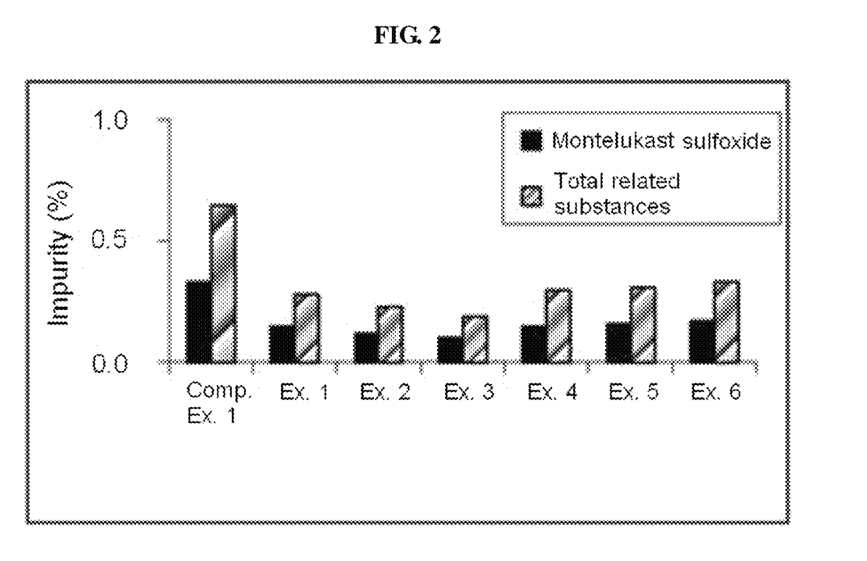
FIG. 2 shows the amount of montelukast related substances for the capsule formulations obtained in Examples 1 to 6 and Comparative Example 1 under accelerated storage condition (40° C./75% RH) for 6 months.
Figure 3:
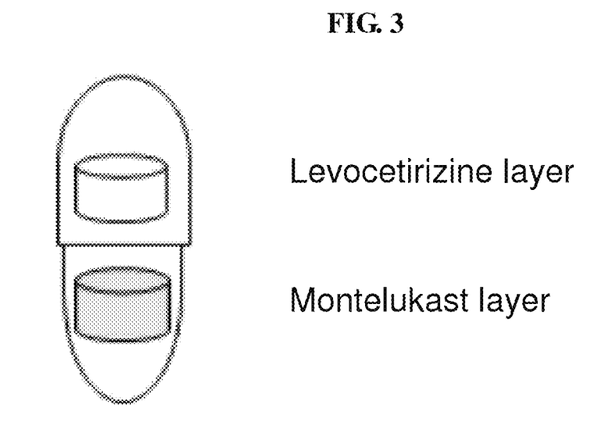
FIG. 3 shows a schematic view of the capsule formulation of the present invention.

As shown in Tables 3 and 4, and FIGS. 1 and 2, the combination capsule formulations of levocetirizine and montelukast which employs an organic acid as a stabilizing agent in accordance with Examples 1 to 6, and the single tablet in accordance with Comparative Example 6 resulted in insignificant changes under the accelerated storage condition after 6 months, and thus exhibited exceptionally good storage stability.

On the contrary, the combination capsule formulations of levocetirizine and montelukast without an organic acid in accordance with Comparative Examples 1 to 3 showed an increase of related substances by approximately 2- to 10-fold as compared to the inventive capsule formulations of Examples 1 to 6 under the accelerated storage condition after 6 months. Also, the combination capsule formulations of levocetirizine and montelukast comprising an inorganic acid, i.e., Comparative Example 4, and comprising an alkalizing agent, i.e., Comparative Example 5 exhibited an increased level of the related substances as compared to the samples comprising an organic acid. Particularly, it was noticeable that samples with an organic acid in accordance with Examples 1 to 6 allowed only a negligible amount of levocetirizine related substance F as compared to other samples. Therefore, it was found that an organic acid as a stabilizing agent can be added to the capsule formulation comprising levocetirizine and montelukast for improving overall stability of the formulation.

While the invention has been described with respect to the above specific embodiments, it should be recognized that various modifications and changes may be made to the invention by those skilled in the art which also fall within the scope of the invention as defined by the appended claims.

What is claimed is:

1. A pharmaceutical formulation for oral administration, which comprises:
   (a) a first tablet comprising levocetirizine or a pharmaceutically acceptable salt thereof and an organic acid; and
   (b) a second tablet comprising montelukast or a pharmaceutically acceptable salt thereof,
   wherein the formulation is a capsule formulation, and the first tablet and the second tablet are contained in a single capsule.

2. The pharmaceutical formulation for oral administration of claim 1, which comprises said organic acid in an amount of 40 to 1000 parts by weight, based on 100 parts of levocetirizine or a pharmaceutically acceptable salt thereof.

3. The pharmaceutical formulation for oral administration of claim 2, which comprises said organic acid in an amount of 50 to 500 parts by weight, based on 100 parts of levocetirizine or a pharmaceutically acceptable salt thereof.

4. The pharmaceutical formulation for oral administration of claim 1, wherein said organic acid is selected from the group consisting of citric acid, tartaric acid, succinic acid, glutamic acid, aspartic acid, oxalic acid, malic acid, acetic acid, sorbic acid, ascorbic acid, alginic acid, fumaric acid, lactic acid and a mixture thereof.

5. The pharmaceutical formulation for oral administration of claim 1, wherein said capsule is a hard capsule.

6. The pharmaceutical formulation for oral administration of claim 5, wherein said capsule is made from a material selected from the group consisting of gelatin, pullulan, hypromellose and polyvinyl alcohol.

7. The pharmaceutical formulation for oral administration of claim 1, wherein said first and second tablets each independently further comprise a pharmaceutically acceptable additive selected from the group consisting of a diluent, a disintegrant, a binder, a lubricant and a mixture thereof.

8. The pharmaceutical formulation for oral administration of claim 1, wherein said first tablet and/or said second tablet further comprises a coating layer.

9. A method for preparing a capsule formulation, which comprises the steps of:
   (i) mixing levocetirizine or a pharmaceutically acceptable salt thereof, a pharmaceutically acceptable additive and an organic acid, and tableting the mixture, wherein the organic acid is employed in an amount of 40 to 1000 parts by weight, based on 100 parts of levocetirizine or a pharmaceutically acceptable salt thereof;
   (ii) mixing montelukast or a pharmaceutically acceptable salt thereof and a pharmaceutically acceptable additive and tableting the mixture; and
   (iii) filling said levocetirizine tablet obtained in step (i) and said montelukast tablet obtained in step (ii) into a hard capsule.

10. The method of claim 9, which further comprises coating said tablet prepared in step (i) and/or (ii).

* * * * *